United States Patent
Labella et al.

(10) Patent No.: US 12,213,820 B2
(45) Date of Patent: Feb. 4, 2025

(54) HIGH RESOLUTION AND HIGH SENSITIVITY PET SCANNER WITH PET DETECTOR MODULES

(71) Applicant: THE RESEARCH FOUNDATION FOR THE STATE UNIVERSITY OF NEW YORK, Albany, NY (US)

(72) Inventors: Andrew Labella, New Rochelle, NY (US); Amirhossein Goldan, Stony Brook, NY (US); Wei Zhao, East Setauket, NY (US); Eric Petersen, Stony Brook, NY (US)

(73) Assignee: THE RESEARCH FOUNDATION FOR THE STATE UNIVERSITY OF NEW YORK, Albany, NY (US)

( * ) Notice: Subject to any disclaimer, the term of this patent is extended or adjusted under 35 U.S.C. 154(b) by 138 days.

(21) Appl. No.: 17/790,088

(22) PCT Filed: Jan. 15, 2021

(86) PCT No.: PCT/US2021/013638
§ 371 (c)(1),
(2) Date: Jun. 29, 2022

(87) PCT Pub. No.: WO2021/146559
PCT Pub. Date: Jul. 22, 2021

(65) Prior Publication Data
US 2023/0052635 A1   Feb. 16, 2023

Related U.S. Application Data

(60) Provisional application No. 62/962,347, filed on Jan. 17, 2020.

(51) Int. Cl.
*A61B 6/42*     (2024.01)
*A61B 6/00*     (2024.01)
(Continued)

(52) U.S. Cl.
CPC ............ *A61B 6/4208* (2013.01); *A61B 6/037* (2013.01); *A61B 6/4488* (2013.01); *A61B 6/461* (2013.01); *G01T 1/202* (2013.01)

(58) Field of Classification Search
None
See application file for complete search history.

(56) References Cited

U.S. PATENT DOCUMENTS

| | | |
|---|---|---|
| 4,531,058 A | 7/1985 | Burnham et al. |
| 6,346,706 B1 | 2/2002 | Rogers et al. |

(Continued)

FOREIGN PATENT DOCUMENTS

| | | |
|---|---|---|
| CN | 1813202 A | 8/2006 |
| CN | 102805630 A | 12/2012 |

(Continued)

OTHER PUBLICATIONS

Labella A. et al., "Prism Mirror Light Guide for Enhanced Gamma Ray Localization in PET", IEEE Nuclear Science Symposium and Medical Imaging Conference, pp. 1-4 (Oct. 26, 2019).

(Continued)

*Primary Examiner* — Edwin C Gunberg
(74) *Attorney, Agent, or Firm* — Scully, Scott, Murphy & Presser, P.C.

(57) ABSTRACT

The disclosure is directed to a device that includes a cavity formed by a plurality of rails, the plurality of rails connected to both a first support and a second support, each at predetermined intervals about a circumference of the first support and the second support; and at least one particle detection device operably connected to each rail of the plurality of rails. The disclosure is also directed to a scanner that includes the device, and a processor.

19 Claims, 6 Drawing Sheets

(51) Int. Cl.
  *A61B 6/03* (2006.01)
  *A61B 6/46* (2024.01)
  *G01T 1/202* (2006.01)

(56) References Cited

U.S. PATENT DOCUMENTS

| | | | |
|---|---|---|---|
| 7,088,901 | B2 | 8/2006 | Kim et al. |
| 7,750,311 | B2 | 7/2010 | Daghighian |
| 8,519,710 | B2 | 8/2013 | Schulz et al. |
| 9,835,737 | B1 | 12/2017 | Czarnecki et al. |
| 2004/0227091 | A1 | 11/2004 | LeBlanc et al. |
| 2006/0241386 | A1* | 10/2006 | Yanagita ............ G01T 1/249 600/415 |
| 2012/0061577 | A1* | 3/2012 | Oleinik ............ G01T 1/20183 250/366 |
| 2012/0068076 | A1 | 3/2012 | Daghighian |
| 2012/0112078 | A1 | 5/2012 | Millett et al. |
| 2013/0009063 | A1 | 1/2013 | Henseler et al. |
| 2013/0256536 | A1 | 10/2013 | Kim |
| 2013/0306876 | A1 | 11/2013 | Uchida |
| 2015/0005616 | A1 | 1/2015 | Saha |
| 2016/0187496 | A1 | 6/2016 | Bradford et al. |
| 2018/0177473 | A1 | 6/2018 | Gregerson et al. |
| 2018/0344274 | A1 | 12/2018 | Berr et al. |
| 2019/0000406 | A1 | 1/2019 | Liu et al. |
| 2019/0142352 | A1 | 5/2019 | Liu et al. |
| 2019/0331810 | A1 | 10/2019 | Yan et al. |
| 2019/0353807 | A1 | 11/2019 | Furenlid et al. |
| 2020/0345322 | A1 | 11/2020 | Bai et al. |
| 2021/0196211 | A9 | 7/2021 | Tai et al. |
| 2022/0120923 | A1 | 4/2022 | Goldan et al. |
| 2022/0211334 | A1 | 7/2022 | Furenlid et al. |
| 2024/0277305 | A1* | 8/2024 | Muelhens ............ A61B 6/4283 |

FOREIGN PATENT DOCUMENTS

| | | |
|---|---|---|
| CN | 105190360 A | 12/2015 |
| CN | 105988152 A | 10/2016 |
| CN | 206725802 U | 12/2017 |
| CN | 111025370 A | 4/2020 |
| CN | 107110980 B | 5/2020 |
| CN | 111443377 A | 7/2020 |
| CN | 112771412 A | 5/2021 |
| CN | 113009548 A | 6/2021 |
| CN | 113069133 A | 7/2021 |
| CN | 113359179 A | 9/2021 |
| CN | 113631960 A | 11/2021 |
| DE | 10 2009 003 792 A1 | 11/2009 |
| EP | 1 627 239 B1 | 10/2006 |
| EP | 1 875 273 B1 | 11/2011 |
| EP | 3 030 154 B1 | 1/2020 |
| EP | 3 924 754 A1 | 12/2021 |
| JP | 9-325185 A | 12/1997 |
| JP | WO2010/070737 A1 | 6/2010 |
| JP | 2011-106981 A | 6/2011 |
| JP | 2012-173128 A | 9/2012 |
| JP | 5080910 B2 | 11/2012 |
| JP | 5104951 B2 | 12/2012 |
| JP | 2013542415 A | 11/2013 |
| JP | 2015-501435 A | 1/2015 |
| JP | 5707269 B2 | 4/2015 |
| JP | 2016-30082 A | 3/2016 |
| JP | 2016-183962 A | 10/2016 |
| JP | 2020-60545 A | 4/2020 |
| WO | 2007/120674 A2 | 10/2007 |
| WO | 2012034220 A1 | 3/2012 |
| WO | 2020/146475 A1 | 7/2020 |
| WO | 2020/168205 A9 | 8/2020 |
| WO | 2021/173708 A1 | 9/2021 |
| WO | 2022/051506 A1 | 3/2022 |
| WO | 2022/051579 A1 | 3/2022 |
| WO | 2020/076643 A1 | 4/2022 |

OTHER PUBLICATIONS

European Extended Supplementary Search Report dated Jan. 23, 2024 received in European Application No. 21 74 1391.3.
International Search Report dated Apr. 22, 2021 issued in PCT/US2021/013638.
Written Opinion dated Apr. 22, 2021 issued in PCT/US2021/013638.
Marcinkowski R. et al., "Optimized Light Sharing for High-Resolution TOF PET Detector Based on Digital Silicon Photomultipliers", Physics in Medicine & Biology 59:7125-7139 (2014).
Song T Y et al., "A Sub-Millimeter Resolution PET Detector Module Using a Multi-Pixel Photon Counter Array", Physics in Medicine & Biology 55:2573-2587 (2010).
Notice of Reasons for Rejection dated Sep. 9, 2024 received in Japanese Patent Application No. 2022-538445.

* cited by examiner

HIGH RESOLUTION AND HIGH SENSITIVITY PET SCANNER WITH PET DETECTOR MODULES

PRIORITY

This application claims priority under 35 U.S.C. § 119 to provisional application U.S. Ser. No. 62/962,347 filed on Jan. 17, 2020, the entire contents of which are incorporated herein by reference.

FIELD

The present disclosure relates generally to the field of radiation imaging and, in particular, to positron emission tomography (PET).

BACKGROUND

Imaging with PET is a powerful technique used primarily for diagnosis, treatment selection, treatment monitoring and research in cancer and neuropsychiatric disorders. Despite its high molecular specificity, quantitative nature and clinical availability, PET has not been able to achieve its full potential as the go-to molecular imaging modality due in large part to its relatively poor spatial resolution, currently on the order of 3-6 mm. With this kind of spatial resolution, the current device cannot possibly measure target density in small nodules and in many human and rodent brain regions relevant to disease etiology and pathophysiology.

Depth-encoding PET detector modules have been developed to mitigate parallax error (mispositioning of the line of response) for long scintillator crystals. This enables small diameter PET rings with reduced component cost per detector ring, large solid angle coverage for increased sensitivity, and reduced contribution of annihilation gamma ray acollinearity on spatial resolution when using crystals with small cross-sectional area. In addition, depth-of-interaction (DOI) information can be used to deconvolve optical photon transport in long crystals, thus improving timing resolution. Depth-encoding detectors based on dual-ended readout achieve the best continuous DOI resolution of <2 mm.

High resolution PET systems such as mammography dedicated Clear-PEM have been developed using dual-ended DOI readout detectors, but these systems are too costly to be commercialized due to the large number of readout electronics compared to standard single-ended readout PET scanners. A recently developed high resolution variant of these detectors shows relatively poor energy and timing resolutions. Alternative single-ended readout detector modules have been proposed, however, in all these designs tradeoffs exists among depth-encoding, cost, scintillator-to-readout coupling ratio, crystal identification accuracy, energy resolution, and timing resolution. To mitigate these tradeoffs, a good depth-encoding detector module is one with single-ended readout where the crystal array is directly coupled to silicon photomultiplier (SiPM) pixels, without any intermediate glass light guide, to minimize sharing of downward traveling scintillation photons across multiple pixels and retain good timing resolution. In addition, upward traveling photons, which do not contribute to the timing information, should be redirected via 180° bending of their paths towards the nearest neighboring SiPMs to retain good energy and DOI resolutions and mimic the behavior of dual-ended depth-encoding readout detectors.

Accordingly, detector modules consisting of depolished multicrystal scintillator arrays coupled 4-to-1 to SiPM pixels on one side and a uniform glass light guide on the opposite side have been investigated in efforts to develop a practical and cost-effective high resolution time-of-flight (TOF) PET scanner, as well as achieve continuous DOI localization using single-ended readout. See, U.S. Pat. No. 10,203,419 to Frazao et al., the contents of which are incorporated herein by reference. In these detector modules, energy weighted average method is utilized for crystal identification to achieve energy and DOI resolutions of 9% and 3 mm full width at half maximum (FWHM), respectively, using 1.53× 1.53×15 mm$^3$ crystals and 3×3 mm$^2$ SiPM pixels. However, these arrays suffer from poor crystal identification along their edges and corners due to the lack of light sharing neighbors, an issue that must be addressed since the edge and corner pixels comprise 75% and 44% of 4×4 and 8×8 SiPM readout chips, respectively. Also, intercrystal light sharing is inefficient when using a uniform glass light guide since many upward traveling photons are reflected back into the primary column and the rest are isotropically shared with a Gaussian intensity distribution amongst neighbors. The problem with isotropic light sharing is the distribution of low-intensity signal across many SiPMs, the integrity of which will be severely affected by dark counts, resulting in degraded energy and DOI resolutions.

Further, other PET detectors have been created, in an attempt to increase DOI resolutions, but these detectors require a cylindrical geometry that must have a diameter large enough to extend over any part of a human's body, which causes readouts to be susceptible to geometrical artifacts.

Thus, what is desired is a PET detector system that can overcome the above deficiencies and be cost efficient. Embodiments of the present disclosure provide devices and methods that address the above needs, and others.

SUMMARY

In one aspect, the disclosure is directed to a device that includes a cavity formed by a plurality of rails, the plurality of rails connected to both a first support and a second support, each at predetermined intervals about a circumference of the first support and the second support; and at least one particle detection device operably connected to each rail of the plurality of rails.

In another aspect, the disclosure is directed to a scanner that includes the device, and a processor.

DETAILED DESCRIPTION

Figure 1:
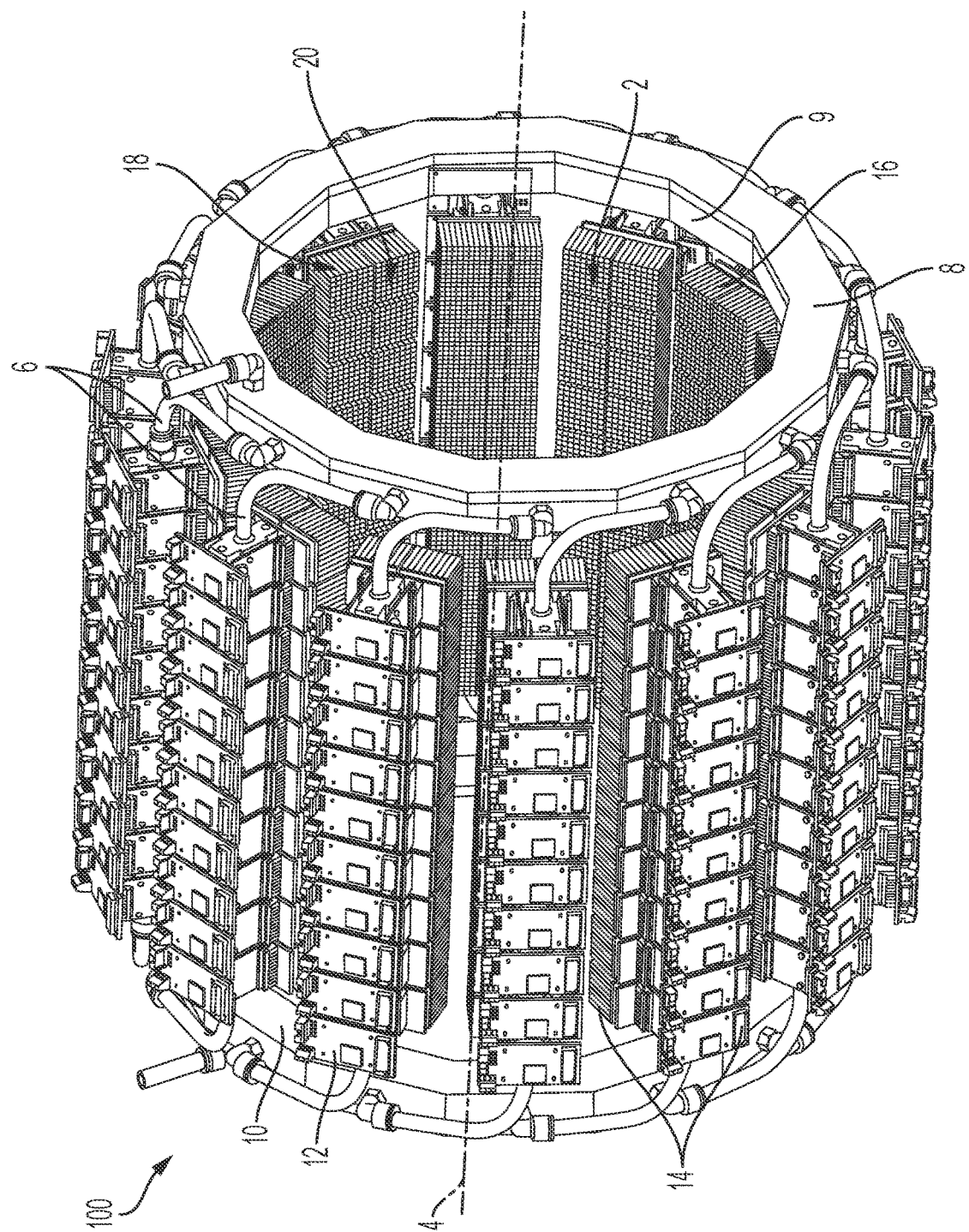
FIG. 1 is a perspective view of a PET device of the present disclosure.

The following detailed description of embodiments of the disclosure are made in reference to the accompanying figures. Explanation about related functions or constructions known in the art are omitted for the sake of clearness in understanding the concept of the invention to avoid obscuring the invention with unnecessary detail. Embodiments of the disclosure described herein provide.

In the discussion and claims herein, the term "about" indicates that the value listed may be somewhat altered, as long as the alteration does not result in nonconformance of the process or device. For example, for some elements the term "about" can refer to a variation of ±0.1%, for other elements, the term "about" can refer to a variation of ±1% or ±10%, or any point therein.

As used herein, the term "substantially", or "substantial", is equally applicable when used in a negative connotation to refer to the complete or near complete lack of an action, characteristic, property, state, structure, item, or result. For example, a surface that is "substantially" flat would either completely flat, or so nearly flat that the effect would be the same as if it were completely flat.

As used herein terms such as "a", "an" and "the" are not intended to refer to only a singular entity, but include the general class of which a specific example may be used for illustration.

As used herein, terms defined in the singular are intended to include those terms defined in the plural and vice versa.

References in the specification to "one embodiment", "certain embodiments", some embodiments" or "an embodiment", indicate that the embodiment(s) described may include a particular feature or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. For purposes of the description hereinafter, the terms "upper", "lower", "right", "left", "vertical", "horizontal", "top", "bottom", and derivatives thereof shall relate to the invention, as it is oriented in the drawing figures. The terms "overlying", "atop", "positioned on" or "positioned atop" means that a first element, is present on a second element, wherein intervening elements interface between the first element and the second element. The term "direct contact" or "attached to" means that a first element, and a second element, are connected without any intermediary element at the interface of the two elements.

Reference herein to any numerical range expressly includes each numerical value (including fractional numbers and whole numbers) encompassed by that range. To illustrate, reference herein to a range of "at least 50" or "at least about 50" includes whole numbers of 50, 51, 52, 53, 54, 55, 56, 57, 58, 59, 60, etc., and fractional numbers 50.1, 50.2 50.3, 50.4, 50.5, 50.6, 50.7, 50.8, 50.9, etc. In a further illustration, reference herein to a range of "less than 50" or "less than about 50" includes whole numbers 49, 48, 47, 46, 45, 44, 43, 42, 41, 40, etc., and fractional numbers 49.9, 49.8, 49.7, 49.6, 49.5, 49.4, 49.3, 49.2, 49.1, 49.0, etc.

A perspective view of a device 100 of the present disclosure is shown in FIG. 1. The device 100 comprises a cavity 2 that extends a distance along an axial length axis 4. The cavity 2 is formed by a plurality of rails 6 (two of which are indicated in FIG. 1), which each extend a distance. In some embodiments the plurality of rails 6 extend a distance that is substantially parallel with the axis 4. The embodiment of the device 100 in FIG. 1 includes fourteen rails 6, however, in other embodiments, the device 100 can include one rail 6, two rails 6 or more, any integer between two and eighteen rails 6 (such as 8 rails 6, 10 rails 6, 12 rails 6, etc.), or nineteen or more rails 6. In some embodiments, a coolant can be transmitted through any portion of each rail 6 and contact one or more portions of each of the particle detection devices 12.

Each of the rails 6 can be an element (such as a rod, pipe, etc.) that is separate from each individual particle detection device 12 (discussed in further detail below) and/or each rail can be formed by joining adjacent detection devices 12 to each other in any suitable way.

The plurality of rails 6 are connected to both a first support 8 and a second support 10 in any suitable way (such as by a mechanical connection, e.g. bolts, rivets, etc. and/or by welding). The plurality of rails 6 are connected to both the first support 8 and the second support 10 at predetermined intervals about a circumference of the first support 8 and the second support 10. These predetermined intervals are determined by the diameter of each of the first support 8 and the second support 10, as well as the number of desired rails 6 for inclusion. Further, the predetermined intervals can be the same interval between adjacent rails, or a variable interval between adjacent rails.

Operably connected to each rail 6 is at least one particle detection device 12. In this embodiment, each rail 6 includes ten particle detection devices 12. However, in other embodiments, each rail 6 can include one particle detection device 12, two particle detection devices 12 or more, any integer between two and twelve particle detection devices 12, or thirteen or more particle detection devices 12. These particle detection devices 12 are discussed in more detail in U.S. patent application Ser. No. 16/899,636, the entire contents of which are incorporated by reference. Each particle detection device 12 includes at least the following components 14: a scintillator array comprising a plurality of scintillator crystals; a plurality of detectors provided on a bottom end of the scintillator array; and a plurality of prismatoids (16) provided on a top end of the scintillator array, wherein each prismatoid of the plurality of prismatoids is configured to redirect particles between top ends of scintillator crystals of the scintillator array, wherein bottom ends of a first group of scintillator crystals of the scintillator array are configured to direct particles to a first detector of the plurality of detectors, and wherein bottom ends of a second group of scintillator crystals of the scintillator array are configured to direct particles to a second detector substantially adjacent to the first detector. Each of these components 12 are discussed in more detail in U.S. patent application Ser. No. 16/899,636, the entire contents of which are incorporated by reference.

The plurality of prismatoids 16 of each of the particle detection devices 12, are oriented towards the cavity 2 of the device 100. Also, the plurality of prismatoids 16 of each of the particle detection devices 12 for each of the plurality of rails 6 form a substantially planar (albeit with variations due to individual prismatoid geometry) prismatoid surface 18, which when the one or more particle detection device 12 are operably connected to the rail 6, form a substantially planar prismatoid rail surface 20. Thus, if the device 100 is of the configuration shown in FIG. 1, there are fourteen substantially planar prismatoid rail surfaces 20.

An internal edge 9 of the first support 8 and an internal edge (not visible from this view) of the second support 10 can include a plurality of substantially flat portions that substantially correspond to each of the substantially planar prismatoid rail surfaces 20. The internal edge of each of the first support 8 and the second support 10 (along with their corresponding substantially planar prismatoid rail surfaces 20)) result in a substantially non-cylindrical geometry of the cavity 2.

Figure 2A:
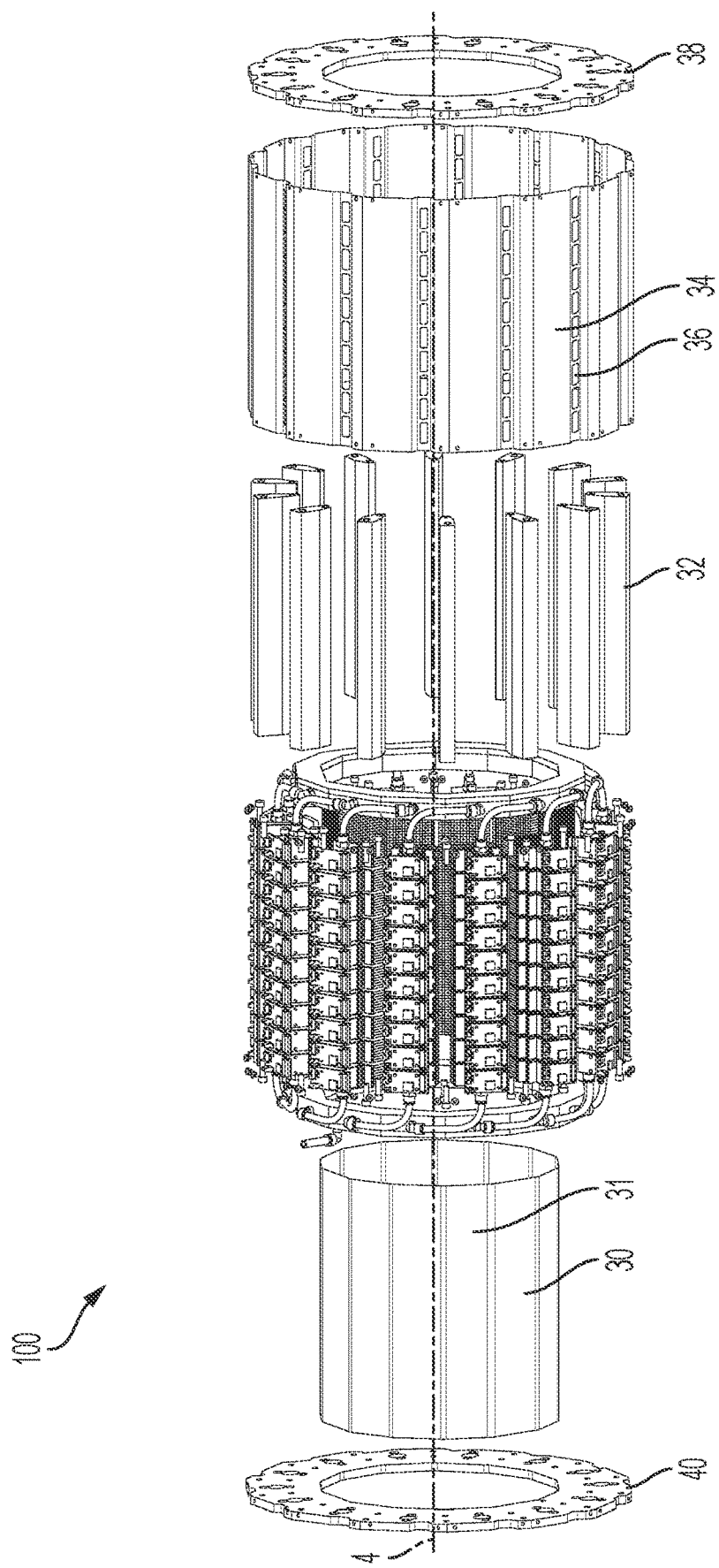
FIG. 2A is an exploded view of the device 100, including additional elements.

An exploded view of the device 100, including additional elements, is shown in FIG. 2A. As can be seen in the embodiment of FIG. 2A, an optional internal shield 30 is configured to be between each of the plurality of particle detection devices 12 and the cavity 2. The internal shield 30 can be formed of any suitable material (e.g. plastic, metal, carbon based materials, ceramics, glass, combinations thereof, etc.) and can be of any suitable thickness. The internal shield 30 can include a plurality of substantially flat panels 31, which can be angled panels of a single piece of material that forms the internal shield 30, or be one or more pieces of material joined together. The substantially flat panels 31 can substantially correspond to each of the substantially planar prismatoid rail surfaces 20.

The dimensions of the internal shield 30, as well as the first support 8 and second support 10 are all configurable, to be dimensioned to substantially surround differing body parts of a mammal, the mammal including but not limited to primates (e.g.; human and nonhuman primates), experimental animals (e.g.; rodents such as mice, rats, etc.), farm animals (such as cows, hogs, sheep, horses etc.), and domestic animals (such as dogs, cats, etc.). One example of a body part the device 100 can be dimensioned for is a mammal's head and/or neck, another example of a body part the device 100 can be dimensioned for is a mammal's torso.

In this context, "dimensioned for" refers to a diameter that is sufficient for the body part to pass through, with a relatively small amount of clearance between the body part and the device. In some embodiments, this dimensioned for can include a more ovular shape instead of a more circular shape, which is illustrated in the figures. For example, if the device 100 is dimensioned for a human's head, the device 100 can be substantially ovular, such that the left-right dimension (minor axis) is smaller than the up-down dimension (major axis), which approximates an ovular cross section of a human's head.

Figure 2B:
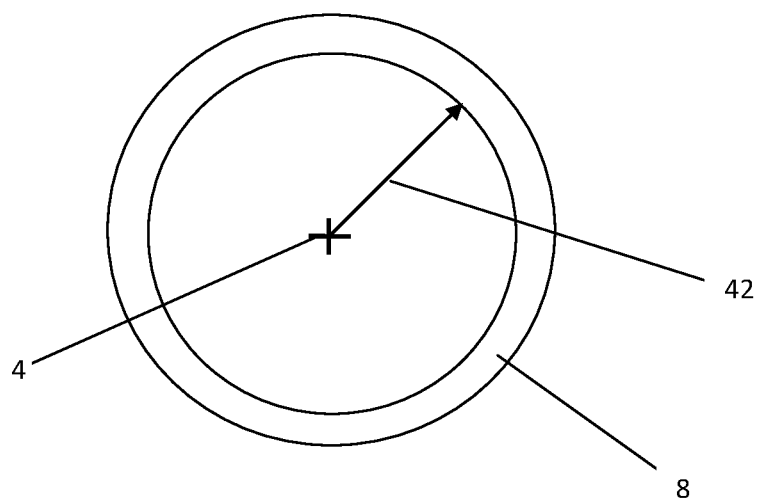
FIGS. 2B and 2C are two cross-sectional views of the device 100.
Figure 2C:
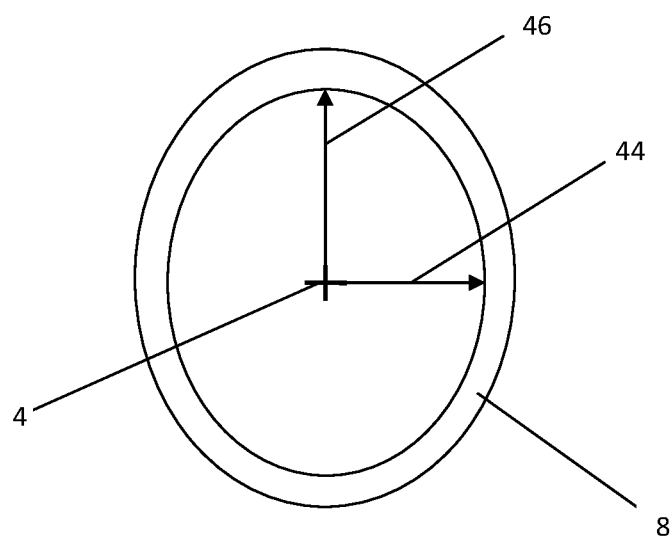

An example of the device with a substantially circular cross-sectional shape is shown in FIG. 2B, with just first support 8 shown for discussion purposes. As can be seen, the shape of the first support 8 is substantially circular, with a substantially constant radius 42. Another embodiment is illustrated in FIG. 2C, with just first support S shown for discussion purposes. As can be seen, the shape of the first support 8 is substantially ovular (or substantially elliptical, or substantially semi-circular or substantially polygonal with a substantially ovular overall shape), with a minor axis 44 that is shorter than a major axis 46. The minor axis 44 can be any amount shorter than the major axis 16, such as about 0.1% shorter, about 0.5% shorter, about 1% shorter, about 2.5% shorter, about 5% shorter, about 7.5% shorter, about 12.5% shorter, about 15% shorter, about 17.5% shorter, about 20% shorter, about 25% shorter, about 30% shorter, about 35% shorter, about 40% shorter, about 50% shorter, about 60% shorter, or more.

In the example of FIG. 2C, if device 100 was to be used for a human's head, the portions of the device 100 near the minor axis 44 would be relatively near the human's ears, while the portions of the device near the major axis 46 would be relatively near the human's forehead and back of head. Further, although FIG. 2C illustrates the minor axis in a substantially horizontal orientation, in other embodiments, both the minor axis and the major axis can be at any rotational point in 360°. In both FIG. 2B as well as 2C, the first support 8 is shown without internal edges 9, but the device 100 could be in either configuration shown in FIGS. 2B and 2C, and still include internal edges 9, such that the device 100 appears to be a polygon, such as a three sided polygon, a four sided polygon, a five sided polygon, a six sided polygon, a seven sided polygon, an eight sided polygon, a nine sided polygon, a ten sided polygon, an eleven sided polygon, a twelve sided polygon, or more sided polygon.

Also as seen in FIG. 2A, between each of the plurality of rails 6, an optional internal guard 32 can extend axially, along axis 4, to substantially separate adjacent rails 6 (and particle detection devices 12 of the adjacent rails 6) from having a line of sight to each other. Although in FIG. 2A the internal guard 32 is shown in between each adjacent rail 6, in other embodiments, only one internal guard 32 is included between a pair of adjacent rails 6. In other embodiments, two or more internal guards 32 are included between two or more, but not all, pairs of adjacent rails 6.

Another element shown in FIG. 2A is an optional external guard 34. The external guard 34 is configured to be between the rails 6 (and their associated one or more particle detection devices 12) and an exterior of the device 100, such that along the axis 4, the optional external guard 34 separates the rails 6 (and their associated one or more particle detection devices 12) from other devices and/or users of the device 100. The external guard 34 can be formed of any suitable material (e.g. plastic, metal, carbon based materials, ceramics, glass, combinations thereof, etc.) and can be of any suitable thickness.

The external guard 34 optionally includes a plurality of openings 36, which as shown in FIG. 2A can be in an axial direction, but in other embodiments, can be in any location and be in any pattern.

The device 100 can also include an optional first cap 38 and/or an optional second cap 40. The first cap 38 and the second cap 40 are substantially orthogonal to axis 4, and each extend circumferentially between a space that is present between the internal shield 30 and the external guard 34, and operably connect to both the internal shield 30 and the external guard 34, when both the internal shield 30 and the external guard 34 are included. In other embodiments, only one of the internal shield 30 and the external guard 34 are present, in such embodiments, the first cap 38 and the second cap 40 are operably connected to either of the internal shield 30 or the external guard 34.

Figure 3:
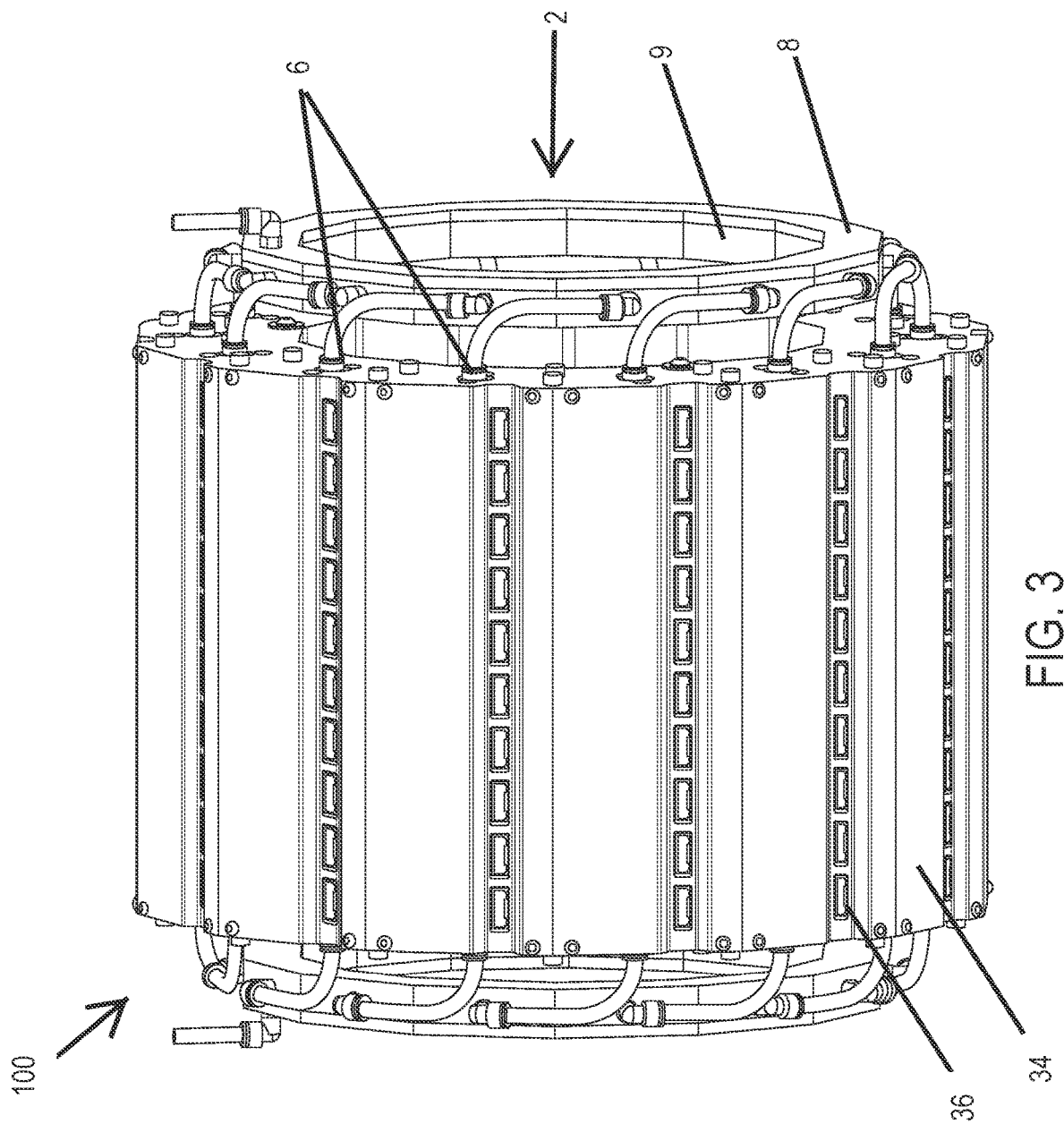
FIG. 3 is a side view of the device 100.

FIG. 3 is a view of device 100, including the additional elements discussed in reference to FIG. 2A. In this view, the device 100, including the external guard 34, are in an operable configuration, which is a configuration that can be included as a portion of a positron emission tomography (PET) scanner for acquiring a PET image, as illustrated in FIG. 4.

Figure 4:
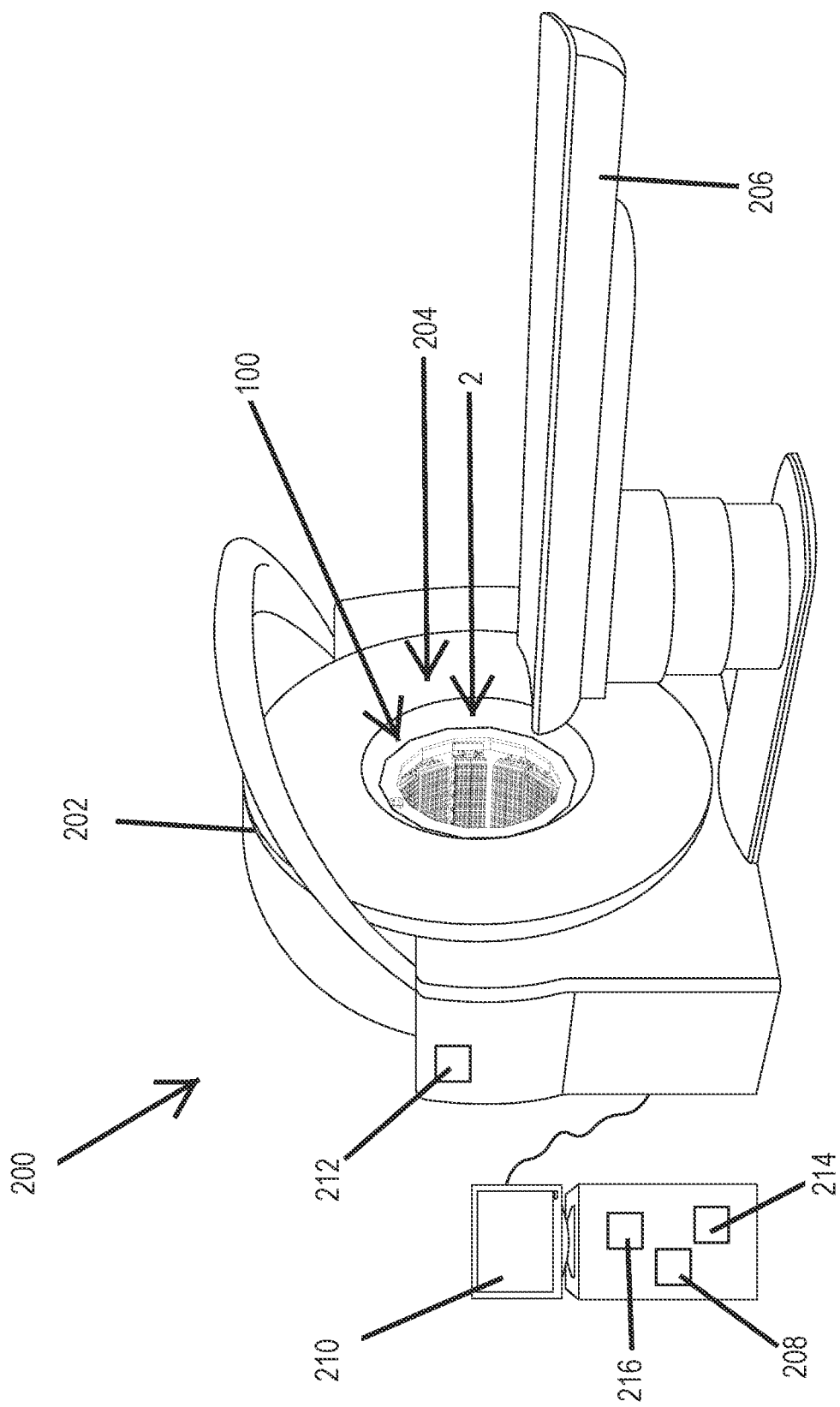
FIG. 4 is a PET scanner that includes the device 100.

As can be seen in FIG. 4, a PET scanner 200 for acquiring a PET image is shown. Shown within a suitable housing 202 of the scanner 202, is the device 100. Within the patient opening 204 (which is substantially coaxial with axis 4 and substantially coexistent with cavity 2) a patient support 206 can be configured to be movable axially (substantially coaxially with axis 4) to expose one or more selected regions of the patient to a PET scan. The PET scan can be acquired in several regions, and depending on the number of patient support 206 positions required to cover the region to be scanned, the complete PET scan may take about 1, about 2, about 5, about 10, about 15, about 20, about 25, about 30, about 35, about 40, about 45, about 50, about 60 or more minutes. The device 100 of the scanner 200 has the capability to scan a combined axial length of up to about 100 cm or more.

The scanner 200 can include, either within the housing 202 of the scanner 200 itself, or in a sufficiently connected (wireless or wired) manner at least one hardware processor 208 that is configured to be in operative communication with each of the plurality of detectors of each of the at least one particle detection devices 12.

The at least one processor 208 is configured to process a plurality of algorithms, examples of which include, but are not limited to supervised machine learning algorithms, configured to perform three dimensional (3D) gamma ray localization of at least one interaction site within at least one scintillator crystal of the plurality of scintillator crystals of one of the at least one particle detection devices 12.

The at least one processor 208 can also be configured to determine a Compton event localization by recovering at least one Compton event scattering among the plurality of scintillator crystals, and localize the at least one Compton event at a scintillator level based on 3D gamma ray localization for each of the at least one particle detection devices 12. The at least one processor 208 can be further configured to perform Depth of Interaction (DOI) localization within the scintillator crystals using an algorithm, such as an energy-weighted algorithm. The at least one processor 208 can be further configured to localize at least one Compton event based on decomposed energies of at least two interactions absorbed in the plurality of scintillator crystals, with the decomposed energies based on at least one light sharing pattern and the at least one light sharing pattern being based on positions of the plurality of scintillator crystals relative to the plurality of detectors and the plurality of prismatoids of each of the particle detection devices 12.

Based on various processes of processor 208 mentioned above, the processor 208 can also be configured to reconstruct a tomographic image, both two dimensional as well as three dimensional, of the region of interest of the patient using any suitable reconstruction algorithm(s).

That reconstructed image can be shown on a display 210. As one example of use of the display 210, the processor 208 can reconstruct the region of the patient or object being scanned from the TOF data. The reconstruction can then be used for three-dimensional rendering, multi-planar reconstruction, or two-dimensional imaging of the function of the tissue of the patient. The images can then be displayed on the display 210. The display 210 can be a CRT, LCD, plasma screen, projector, printer, or other output device for showing an image, and can be sufficiently connected (wireless or wired) manner with the at least one processor 208.

Further, the scanner can include a control device 212 that can be configured to control the scanner 200 and device 100. The control device 212 can have a storage medium 214 on which computer programs for controlling the scanner 200 and device 100 are executably stored. The scanner 200 also has an input 216 for entering control information, e.g. imaging parameters and examination parameters, and an output for outputting control information and reconstructed images.

Figure 5:
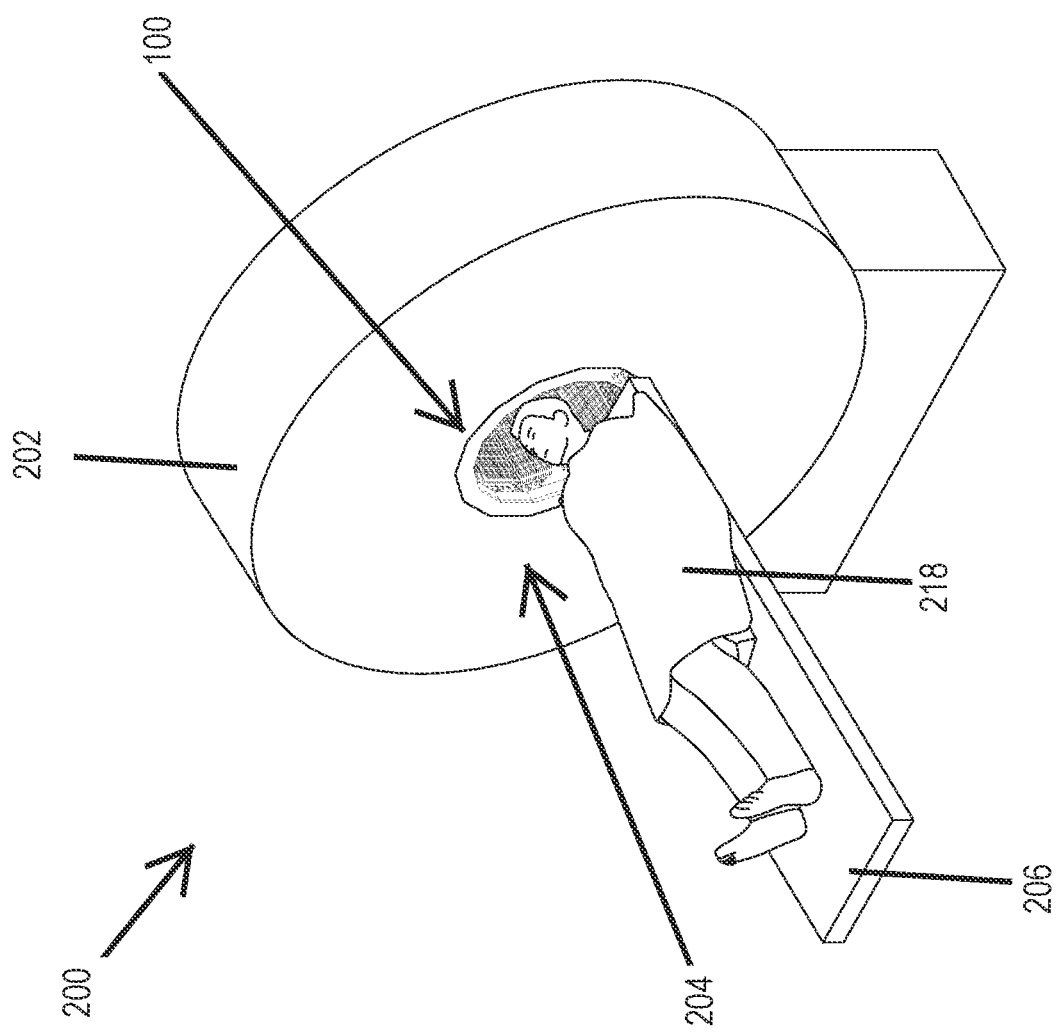
FIG. 5 is a PET scanner that includes the device 100 and a patient.

Scanner 200 is also shown in FIG. 5, with a human patient 218 being supported by patient support 206. In this example, the head of the patient 218 has been inserted into the patient opening 204, in preparation of a PET scan of the patient's 218 head.

In this application, including the definitions below, the term 'processor' or the term 'controller' may be replaced with the term 'circuit.' The term 'processor' may refer to, be part of, or include processor hardware (shared, dedicated, or group) that executes code and memory hardware (shared, dedicated, or group) that stores code executed by the processor hardware.

The processor may include one or more interface circuits. In some examples, the interface circuits may include wired or wireless interfaces that are connected to a local area network (LAN), the Internet, a wide area network (WAN), or combinations thereof. The functionality of any given processor of the present disclosure may be distributed among multiple processors that are connected via interface circuits. For example, multiple processors may allow load balancing. In a further example, a server (also known as remote, or cloud) processor may accomplish some or all functionality on behalf of a client processor.

Further, at least one embodiment of the invention relates to a non-transitory computer-readable storage medium comprising electronically readable control information stored thereon, configured in such that when the storage medium is used in a controller of a magnetic resonance device, at least one embodiment of the method is carried out.

Even further, any of the aforementioned methods may be embodied in the form of a program. The program may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The described embodiments and examples of the present disclosure are intended to be illustrative rather than restrictive, and are not intended to represent every embodiment or example of the present disclosure. While the fundamental novel features of the disclosure as applied to various specific embodiments thereof have been shown, described and pointed out, it will also be understood that various omissions, substitutions and changes in the form and details of the devices illustrated and in their operation, may be made by those skilled in the art without departing from the spirit of the disclosure. For example, it is expressly intended that all combinations of those elements and/or method steps which perform substantially the same function in substantially the same way to achieve the same results are within the scope of the disclosure. Moreover, it should be recognized that structures and/or elements and/or method steps shown and/or described in connection with any disclosed form or embodiment of the disclosure may be incorporated in any other disclosed or described or suggested form or embodiment as a general matter of design choice. Further, various modifications and variations can be made without departing from the spirit or scope of the disclosure as set forth in the following claims both literally and in equivalents recognized in law.

What is claimed is:

1. A device, the device comprising:
   a first support;
   a second support spaced from the first support in an axial direction;
   a plurality of rails each respectively connected to an exterior-facing side of the first support and an exterior-facing side of the second support, the plurality of rails extending between the first support and the second support where at least a part of the plurality of rails is orthogonal to the first support and the second support, the plurality of rails, the first support and the second support defining a cavity, the exterior-facing side of the first support and the exterior-facing side of the second support being a side opposite to a side of the first support and a side of the second support facing the cavity, the rails being disposed at predetermined intervals about a circumference of the first support and the second support; and
      a plurality of particle detection devices operably connected to each rail of the plurality of rails in a row of particle detection devices, where a respective rail overlaps at least part of the row of particle detection devices in a radial direction, each particle detection device comprising:
         a scintillator array comprising a plurality of scintillator crystals;
         a plurality of detectors provided on a bottom end of the scintillator array; and
         a plurality of prismatoids provided on a top end of the scintillator array, wherein each prismatoid of the plurality of prismatoids is configured to redirect particles between top ends of scintillator crystals of the scintillator array,
      wherein bottom ends of a first group of scintillator crystals of the scintillator array are configured to direct particles to a first detector of the plurality of detectors, and
      wherein bottom ends of a second group of scintillator crystals of the scintillator array are configured to direct particles to a second detector substantially adjacent to the first detector,
      wherein the plurality of prismatoids of each particle detection device is oriented towards the cavity.

2. The device of claim 1, wherein each row of particle detection devices comprises multiple aligned particle detection devices.

3. The device of claim 1, wherein the plurality of rails comprises at least four rails.

4. The device of claim 1, further comprising an internal shield configured to be between the plurality of particle detection devices and the cavity.

5. The device of claim 4, further comprising an external guard that extends axially.

6. The device of claim 5, further comprising a first cap and a second cap, wherein the first cap and the second cap each extend circumferentially between a space between the internal shield and the external guard.

7. The device of claim 5, wherein the rows of particle detection devices are between the internal shield and the external guard in the radial direction.

8. The device of claim 1, further comprising a plurality of internal guards, wherein each of the plurality of internal guards extend axially between two of the plurality of rails.

9. The device of claim 8, wherein each of the plurality of internal guards further provides a barrier between rows of particle detection devices in different rails.

10. The device of claim 1, wherein the cavity is dimensioned to extend about a mammal's head.

11. The device of claim 1, wherein the cavity is dimensioned to extend about a mammal's torso.

12. The device of claim 1, wherein the each prismatoid is substantially shaped as at least one of at least one prism, at least one antiprism, at least one frustum, at least one triangle, at least one cupola, at least one parallelepiped, at least one wedge, at least one pyramid, at least one truncated pyramid, and at least one portion of a sphere.

13. The device of claim 1, wherein the device has a substantially ovular cross section.

14. A positron emission tomography (PET) scanner for acquiring a PET image, the scanner comprising:
   the device of claim 1; and
   at least one processor in operative communication with the plurality of detectors of each of the plurality of particle detection devices, wherein the at least one processor comprises a plurality of algorithms configured to perform three dimensional (3D) gamma ray localization of at least one interaction site within at least one scintillator crystal of the plurality of scintillator crystals.

15. The scanner of claim 14, wherein the at least one processor is further configured to determine a Compton event localization.

16. The scanner of claim 14, wherein the at least one processor is configured to perform Depth of Interaction (DOI) localization within the scintillator crystals using an energy-weighted algorithm.

17. The scanner of claim 14, further comprising a patient support that is configured to move axially within the scanner.

18. The scanner of claim 14, further comprising a display for displaying the PET image.

19. The scanner of claim 14, further comprising a coolant system configured to deliver a coolant to each of the plurality of particle detection devices via the rails.

\* \* \* \* \*